United States Patent [19]

Kadaba

[11] Patent Number: 4,610,994
[45] Date of Patent: Sep. 9, 1986

[54] 1,2,3-TRIAZOLE ANTICONVULSANT DRUGS

[75] Inventor: Pankaja K. Kadaba, Lexington, Ky.

[73] Assignee: The University of Kentucky Research Foundation, Lexington, Ky.

[21] Appl. No.: 604,026

[22] Filed: Apr. 26, 1984

[51] Int. Cl.$^4$ .................... C07D 401/04; A61K 31/41
[52] U.S. Cl. ..................................... 514/340; 514/359; 546/276; 548/255
[58] Field of Search ....................... 546/276; 548/255; 424/263, 269; 514/340, 359

[56] References Cited

U.S. PATENT DOCUMENTS 3,470,196  9/1969  Harvey ................................. 548/255
4,013,441  3/1977  Bianchetti et al. ................... 548/255
4,474,599  10/1984 Rogers et al. ....................... 546/276

FOREIGN PATENT DOCUMENTS 2070607  9/1981  United Kingdom .

OTHER PUBLICATIONS

Kadaba, Synthesis, Sep. 1978, pp. 694–695.

Kadaba, Jour. F. Prakt Chemie., Band 324, Heft 5, 1982, S. 857–864.

Primary Examiner—Jane T. Fan
Attorney, Agent, or Firm—Lowe, Price, LeBlanc, Becker & Shur

[57] ABSTRACT

Anticonvulsant compositions comprise as the active ingredient a compound selected from the group consisting of those of the formulae:

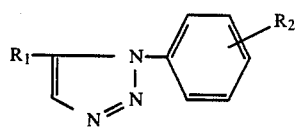

wherein $R_1$ is phenyl, 4-pyridyl, 3-pyridyl, or 2-pyridyl, and $R_2$ is hydrogen, m- or p-methyl, p-methoxy, m- or p-chloro, m- or p-bromo, m- or p-fluoro, m- or p-trifluoromethyl, 3,4-dichloro or 3,5-dichloro. The compositions are administered to mammals in an amount to provide a dosage amount ranging from about 25 mg/kg to 300 mg/kg.

35 Claims, No Drawings

1,2,3-TRIAZOLE ANTICONVULSANT DRUGS

TECHNICAL FIELD

This invention relates to 1H-1,2,3-triazoles and their use as a novel class of anticonvulsant drugs, and more particularly relates to certain additional new 1H-1,2,3-triazoles, their methods of preparation, and compositions for their use in the treatment of convulsive disorders.

BACKGROUND ART

Studies over the past 15 years suggest that the prevailing rate of epilepsy in the United States is between 5 and 20 per 1000, and recent estimates drawn from population surveys indicate that the higher rates are closer to the true prevalence. This means that 1 to 4 million Americans suffer from some form of epilepsy. For certain types of seizures there are no specific drugs available; for seizures that are controlled with currently available therapy, a new drug may allow a reduction in the toxic side effects. Despite these facts, between 1960 and 1974, no new anticonvulsant drug was marketed in the United States (with the exception of diazepam, which was marketed primarily as a minor tranquilizer) (Vida, J. A. "Anticonvulsants," *Academic Press*, New York, 1977). However, since the approval of carbamazepine in 1974 and clonazepam in 1975, and sodium dipropylacetate, eterobarb, mexiletine and others in 1977–1978, there has been a resurgence of interest in the development of better anticonvulsant drugs for the management of epilepsy. Also responsible for this renewed interest is the establishment of the Anticonvulsant Screening Project of the Antiepileptic Drug Development (ADD) Program of NINCDS (National Institute of Neurological and Communicative Disorders and Stroke) of NIH, in January, 1975.

In recent years hundreds of different heterocyclic compounds have been synthesized and screened for anticonvulsant activity. These include mostly five and six membered ring systems containing up to three or four heteroatoms and seven membered ring systems related to the diazepines. Among the nitrogen containing heterocycles, a considerable amount of work has been done in the areas of five membered rings bearing one or two nitrogen atoms.

Five membered rings with 3 or 4 nitrogen atoms that have been investigated, include mostly, 1,2,4-triazoles and some tetrazoles. Very little has been done on 1H-1,2,3-triazoles (Popp, F. D., In "Anticonvulsants," J. A. Vida, Ed. *Academic Press*, New York, 1977).

The literature indicates that to date there are only two references relating to studies on the anticonvulsant potential of 1H-1,2,3-triazoles. Unlike the simple 1-5-substituted-1,2,3-triazoles of this invention, both these references are to fused ring benzotriazoles of the structures I and II shown below by Gilbert and Rumanowski (Gilbert, E. E.,

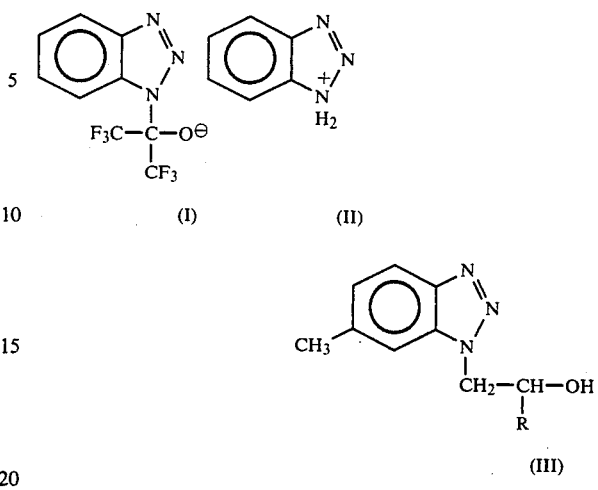

and Rumanowski, E. J., U.S. Pat. No. 3,592,822, 1971) and structure III by Wolf (Wolf, M., U.S. Pat. No. 3,394,143, 1968). In addition certain substituted 1H-1,2,3-triazoles IV and V have been shown to afford some degree of protection against oxotremorin induced tremors in mice at 100 mg/kg. (Miller, A. D.,

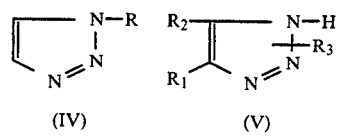

I CI, United States, Ger. Pat. No. 2,648,826 (Cl. C07D249/04), 05 May, 1977; U.S. application No. 626,140, 26th Oct., 1975, 53 pages) and (ICI Americas, Inc., Belg. 853,978 (Cl. C07D), 26th Oct. 1977, Appl. 26th Apr. 1977, 11 pages). Compounds of the type IV and V have been investigated as potential tranquilizers or antianxiety agents but not as anticonvulsants.

The 1,2,3-triazoles are a novel group of anticonvulsant compounds because their heterocyclic ring system is different from that of conventional anticonvulsant drugs. The presently marketed antiepileptic drugs, for the major part, have a dicarboximide function and/or a disubstituted quaternary carbon group (barbiturates, hydantoins, succinimides, oxazolidinediones) or closely related structure (pyrimidone). On the other hand, the dicarboximide function, which contributes to the inherent hypnotic and sedative activity of the barbiturates and related compounds, is absent in the triazoles.

The chemistry of 1,2,3-triazoles has been extensively studied (Gilchrist, T. L., and Gymer, G. E., "Advances in Heterocyclic Chemistry" Vol. 16, 1974, pp. 33–85; Benson, F. R., and Savell, W. L., Chemical Reviews, 46, 1, 1950; Boyer, J. H., in "Heterocyclic Compounds", Edited by R. C. Elderfield, Vol. 1, p. 384–461, Wiley, New York, 1961), which also include the applicant's own publications on the synthesis of 1-aryl-5-heteroaryl-substituted 1H-1,2,3-triazoles. However, with the exception of the few 1,2,3-triazoles mentioned earlier, no studies have been conducted on 1,2,3-triazoles for use as anticonvulsants.

As indicated, the present applicant has published two papers involving her work on triazoles. The publications discuss primarily a convenient general synthetic route for the preparation of 1,5-substituted 1,2,3- triazoles by permanganate oxidation of the respective triazolines. (Kadaba, P. K. "Synthesis, International Journal of Methods in Synthetic Organic Chemistry," No. 9: September, 1978, pp. 694–695). (Kadaba, P. K., "Journal fur praktische Chemie," Vol. 324, 1982, pp. 857–864.)

In both these publications, however, there is no disclosure of the use of any of the 1,2,3-triazole compounds as anticonvulsants.

SUMMARY OF THE INVENTION

It is accordingly one object of the present invention to provide certain triazoles as anticonvulsant drugs.

A further object of the present invention is to provide several new 1H-1,2,3-triazoles and methods for their use in the treatment of convulsive disorders.

A still further object of the present invention is to provide anticonvulsant compositions containing as the essential ingredient certain 1H-1,2,3-triazoles and use of these triazoles as antiepileptic drugs in the treatment of convulsive disorders such as epilepsy.

Other objects and advantages of the present invention will become apparent as the description thereof proceeds.

In satisfaction of the foregoing objects and advantages, there is provided by this invention anticonvulsant compositions comprising as the active ingredient, a compound selected from those of the following formulae:

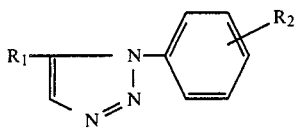

wherein $R_1$ is phenyl, 4-pyridyl, 3-pyridyl, or 2-pyridyl, and $R_2$ is hydrogen, m- or p-methyl, p-methoxy, m- or p-fluoro, m- or p-chloro, m- or p-bromo, m- or p-trifluoromethyl, 3,4-dichloro, or 3,5-dichloro substituent.

Also provided are methods for administration of the anticonvulsant compositions of this invention to mammals in the treatment of convulsive disorders such as epilepsy including petit mal and grand mal.

There is also provided by this invention certain new compounds which are useful as anticonvulsant drugs. These compounds may be characterized by the following general formulae:

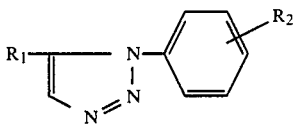

wherein $R_1$ is 4-pyridyl, or 3-pyridyl, and $R_2$ is m-methyl, m- or p-fluoro, m- or p-chloro, m- or p-bromo, m- or p-trifluoromethyl, 3,4-dichloro, or 3,5-dichloro.

DESCRIPTION OF PREFERRED EMBODIMENTS

As indicated above, this invention relates to certain 1,2,3-triazoles which are useful as anticonvulsants. The triazoles of this invention are to be named as 1H-1,2,3-triazoles. The triazoles of this invention are substituted in the 1 and 5 positions by aryl or heterocyclic groups which may also contain substituents. The triazole compounds of this invention have potent to moderate anticonvulsant activity as antiepileptic drugs in the treatment of convulsive disorders such as petit mal (absence seizures) and grand mal (major motor seizures).

In one aspect of the invention, it relates to novel anticonvulsant compositions which comprise as the active ingredient a compound selected from those of the following formulae:

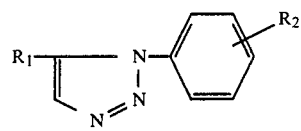

wherein $R_1$ is phenyl, 4-pyridyl, 3-pyridyl, or 2-pyridyl, and $R_2$ is hydrogen, m- or p-methyl, p-methoxy, m- or p-fluoro, m- or p-chloro, m- or p-bromo, m- or p-trifluoro methyl, 3,4-dichloro or 3,5, dichloro substituents.

In a further aspect of the present invention, new compounds are provided which have anticonvulsant activity and which are of the following general formulae:

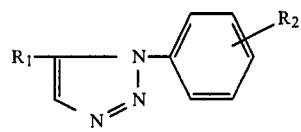

In the above formulae, $R_1$ is 3-pyridyl, or 4-pyridyl, and $R_2$ is m-methyl, m- or p-fluoro, m- or p-bromo, m- or p-chloro, m- or p-trifluoromethyl, 3,4-dichloro, or 3,5-dichloro substituent.

There is further provided by this invention methods for administration of the anticonvulsant composition to mammals including animals and humans.

The triazoles of this invention may be prepared by the oxidation of 4,5-dihydro-1H-1,2,3-triazoles ($\Delta^2$-1,2,3-triazolines), which in turn, are prepared by the reaction of diazomethane with Schiff bases as described, for example, by Mustafa, A., (J. Chem. Soc.), 234 (1949), and by Buckley, G. D., (J. Chem. Soc), 1850, (1954). Further methods of preparation of 1,2,3-triazolines involving 1,3-dipolar cycloaddition reactions are described in the applicant's own publications in Kadaba, et al. (J. Org. Chem. 26, 2331 (1961), by Kadaba in "Tetrahedron," 22, 2453 (1966), by Kadaba in "Tetrahedron," 25, 3053 (1969) and J. Heterocyclic Chem., 12, 143, (1975). This reaction proceeds generally in accordance with the following equation. (Eq. 1)

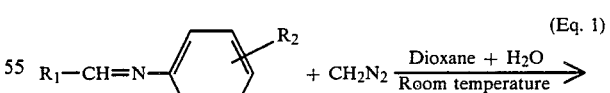  (Eq. 1)

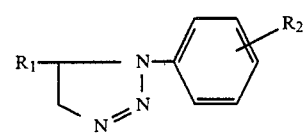

$\Delta^2$-1,2,3-Triazolines

In the above equation $R_1$ and $R_2$ are as defined above.

Kinetic studies on solvent effects of this reaction indicate that protic solvents such as water have a general accelerating effect on the reaction and by carrying out the addition reaction in an aqueous dioxane solution, high yields of triazolines are produced.

The 1,2,3-triazolines undergo smooth oxidation to 1,2,3-triazoles, using potassium permanganate in a two-phase system (benzene-water or chloroform-water), in the presence of a phase-transfer catalyst such as tetrabutylammonium chloride (Kadaba, P. K., Synthesis, 694, 1978 and Kadaba, P. K., J. prakt. Chem., 324, 857, 1982) in accordance with the following equation. (Equation 2)

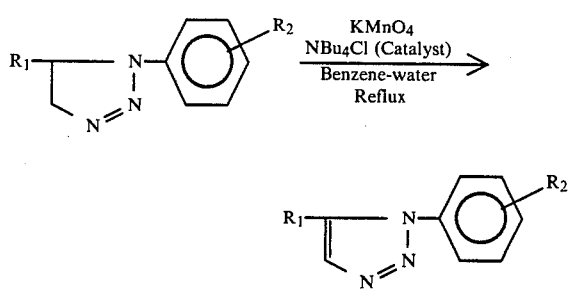

The permanganate oxidation of triazolines to triazoles provides a general method for the synthesis of both 1,5-diaryl and 1-aryl-5-heteroaryl substituted 1H-1,2,3-triazoles. The reaction is superior to triazole synthesis by azide addition to acetylenes. The lack of reactivity of acetylenes as well as the formation of isomeric 1,4- and 1,5-substituted triazoles in the cycloaddition of phenyl azide to aryl acetylenes limit the utility of the acetylene-azide addition reaction in triazole synthesis. (Gilchrist, T. L., and Gymer, G. E., Adv. Heterocycl. Chem., 16, 33, 1974; Stephan, E., Bull Soc. Chim., Fr., 7-8, 364, 1978; L'abbe, G. and Hassner, A., Bull. Soc. Chim Belg. 80, 209, 1971; Alonso, G., Garcia-Lopez, M. T., Garcia-Munoz, G., Madronero, R., and Rico, M., *J. Heterocycl. Chem.*, 7, 1269, 1970).

As pointed out, the triazole compounds and resulting anticonvulsant compositions of this invention are useful in the treatment of convulsive disorders. The potency of the compounds range from those which are very potent to those of moderate potency. A series of triazoles of this invention has been evaluated in Phase I anticonvulsant screening using two seizure models in the mouse, the maximal electro-shock seizure (MES) test and the subcutaneous pentylenetetrazole (Metrazole) seizure threshold (scMet) test. These two methods of seizure provocation elicit reliably well characterized seizure phenomena (Chen. G., et al. Proc. Soc. Exp. Biol. Med., 87, 334 (1954), and together have been shown sufficient to identify all compounds known to demonstrate anticonvulsant activity in other tests. Based on the Phase I screening results, the compound tested is placed in one of three categories. Those failing to demonstrate anticonvulsant activity at doses up to 300 mg/kg are considered inactive. Class II compounds show anticonvulsant activity at doses greater than 100 mg/kg or show activity at 100 mg/kg which is not reinforced by similar activity at 300 mg/kg. Thus compounds of Class or Group II demonstrate anticonvulsant activity without signs of neurological deficit, but do not have significant potency. The Class I compounds are those which are most promising as anticonvulsants. They demonstrate anticonvulsant activity in either the MES test or the scMet test, or both at doses of 100 mg/kg or 30 mg/kg without signs of neurological deficit and thus have an estimated protective index of greater than 1.

The following table presents the results of these tests with respect to certain compounds of the present invention. This Table 1 identifies the specific compounds tested by chemical name, and provides the anticonvulsant activity based on classification in Group I or Group II.

TABLE I

| Compound | Anticonvulsant Activity Group Classification |
|---|---|
| 1. 1-(p-Chlorophenyl)-5-phenyl-1H—1,2,3-triazole | I |
| 2. 1-(p-Bromophenyl)-5-phenyl-1H—1,2,3-triazole | I |
| 3. 1-Phenyl-5-(4-pyridyl)-1H—1,2,3-trizole | I |
| 4. 1-(p-Fluorophenyl)-5-(4-pyridyl)-1H—1,2,3-triazole | II |
| 5. 1-(p-Tolyl)-5-(4-pyridyl)-1H—1,2,3-triazole | II |
| 6. 1-(p-Anisyl)-5-(4-pyridyl)-1H—1,2,3-triazole | II |
| 7. 1-(m-Chlorophenyl)-5-(4-pyridyl)-1H—1,2,3-triazole | I |
| 8. 1-(3,4-Dichlorophenyl)-5-(4-pyridyl)-1H—1,2,3-triazole | II |
| 9. 1-(3,5-Dichlorophenyl)-5-(4-pyridyl)-1H—1,2,3-triazole | I |
| 10. 1-(p-Chlorophenyl)-5-(3-pyridyl)-1H—1,2,3-triazole | I |
| 11. 1-(p-Bromopheny)-5-(3-pyridyl)-1H—1,2,3-triazole | I |
| 12. 1-(p-Fluorophenyl)-5-(3-pyridyl)-1H—1,2,3-triazole | I |
| 13. 1-(3,4-Dichlorophenyl)-5-(3-pyridyl)-1H—1,2,3-triazole | II |
| 14. 1-(p-Chlorophenyl)-5-(2-pyridyl)-1H—1,2,3-triazole | I |
| 15. 1-(m-Fluorophenyl)-5-(4-pyridyl)-1H—1,2,3-triazole | I |
| 16. 1-(m-Bromophenyl)-5-(4-pyridyl)-1H—1,2,3-triazole | I |
| 17. 1-(m-Tolyl)-5-(4-pyridyl)-1H—1,2,3-triazole | II |
| 18. 1-(m-Trifluoromethylphenyl)-5-(4-pyridyl)-1H—1,2,3-triazole | I |
| 19. 1-(p-Trifluoromethylphenyl)-5-(3-pyridyl)-1H—1,2,3-triazole | II |

As shown in the above table, the most potent compounds are compounds 1,2,3,7,9,10,11,12 and 14. These compounds belong to Class I and with the exception of compounds 7 and 9, the remaining seven compounds do not exhibit significant signs of neurological deficit at their effective dose levels. In addition, compounds 8 and 13 in Class II are also effective anticonvulsant compounds because they give 100% protection at 300 mg/kg, without any signs of neurological deficit. Thus, these nine compounds, 1,2,3,8,10,11,12,13 and 14, represent the preferred embodiments of the anticonvulsant compositions of this invention. Compound 10 which is 1-(para-chlorophenyl)-5-(3-pyridyl)-1H-1,2,3-triazole and Compound 11 which is 1-(p-bromophenyl)-5-(3-pyridyl)-1H-1,2,3-triazole are the most preferred compounds of this invention.

As indicated above, although other preparative reactions could be used for the triazoles of this invention, the permanganate oxidation of 1,2,3-triazolines in a phase-transfer catalyzed reaction is the method of choice for the synthesis of 1,5-substituted triazoles, especially 1-aryl-5-heteroaryl-1H-1,2,3-triazoles (Equation 2). Several 1-aryl-5-heteroaryl-1,2,3-triazoles were prepared for the first time by this method (P. K. Kadaba, Synthesis, 694, 1978).

A mixture of 1,2,3-triazoline (0.005 mol) in benzene (75 ml), potassium permanganate (0.025 mol) in water (100 ml) and tetrabutylammonium chloride (0.5 mmol) was heated under reflux with magnetic stirring for 4 hours or more. The reaction mixture was then cooled to room temperature, treated with sodium sulfite to destroy excess potassium permanganate and filtered under suction to remove the manganese dioxide. The residue was washed twice with hot benzene and combined with benzene extracts of the filtrate, washed with water, dried, and evaporated under reduced pressure. An oily residue was obtained, which upon cooling and trituration with diethylether, yielded the triazole as a crystalline solid. Recrystallization from diethyl ether or a mixture of petroleum ether and acetone or methanol yielded the analytically pure products. Chloroform can easily be used in place of benzene in certain reactions.

Furthermore, since Schiff bases (imines) bearing a range of aromatic or heterocyclic substituents can be readily prepared, the $CH_2N_2$-imine reaction is particularly suited for the synthesis of the various 1,5-substituted triazolines required for the oxidation reaction. The addition of diazomethane to imines occurs regioselectively and thus there is no problem of isomeric triazole formation as in azide-acetylene addition reactions. As pointed out above, this addition is preferably carried out in aqueous dioxane solutions according to the applicant's previous publications. In a typical preparation, the Schiff base is dissolved in a cold, freshly prepared solution of $CH_2N_2$ in wet dioxane. The reaction mixture is then allowed to stand at 15°–20° C. for 2–4 days in the case of the reactive anils and 6–7 days in the case of the slow reactions. At the end of this period, the mixture is cooled and diluted with water to precipitate the triazoline adduct.

The $CH_2N_2$ for the reaction is prepared conveniently from N,N'-nitrosomethylurea in the same manner that undistilled ethereal solutions are obtained, but using 1,4-dioxane in place of diethyl ether. Dioxane is the solvent of choice because of its easy miscibility with water and the ease with which it can be substituted for diethyl ether. The $CH_2N_2$ solution thus obtained contains water in sufficient amounts to catalyze the reaction and is used immediately.

The Schiff bases are prepared using standard procedures by heating a mixture of the appropriate adehyde and amine in ethanol or alternatively by heating the mixture in benzene followed by azeotropic removal of the water, the latter being a more suitable procedure in difficult cases.

The anticonvulsant compounds of the present invention may be administered to animals or humans at doses ranging from about 25 mg/kg up to about 300 mg/kg. Preferred levels of administration range from about 25 mg/kg up to 100 mg/kg. The active ingredients or compounds of this invention may be administered in any desired form by injection or in the oral form. Conventional adjuvents and carriers may be employed in combination with about 0.001 to 2.0 wt.% of the active ingredient. Thus the anticonvulsant compositions of this invention may be administered in pill form or by injection. As indicated above, the dosage rate ranges from about 25 mg/kg up to about 300 mg/kg.

The following examples are presented to illustrate the invention but it is not to be considered as limited thereto. In the examples and throughout the specification, parts are by weight unless otherwise indicated.

EXAMPLE 1

Using the reaction of Equation 2 described above involving potassium permanganate oxidation of 1,2,3-triazolines, the following compounds were prepared. In the following Table 2, melting points and yields are given for new compounds prepared.

TABLE 2

| Compound | M. Pt. °C. | Yield % |
|---|---|---|
| 1. 1-(p-Chlorophenyl)-5-phenyl-1H—1,2,3-triazole | — | — |
| 2. 1-(p-Bromophenyl)-5-phenyl-1H—1,2,3-triazole | — | — |
| 3. 1-Phenyl-5-(4-pyridyl)-1H—1,2,3-triazole | — | — |
| 4. 1-(p-Fluorophenyl)-5-(4-pyridyl)-1H—1,2,3-triazole | 154–156 | 67 |
| 5. 1-(p-Tolyl)-5-(4-pyridyl)-1H—1,2,3-triazole | — | — |
| 6. 1-(p-Anisyl)-5-(4-pyridyl)-1H—1,2,3-triazole | — | — |
| 7. 1-(m-Chloro-phenyl)-5-(4-pyridyl)-1H—1,2,3-triazole | 109–100.5 | 40 |
| 8. 1-(3,4-Dichlorophenyl)-5-(4-pyridyl)-1H—1,2,3-triazole | 139–140 | 60 |
| 9. 1-(3,5-Dichlorophenyl)-5-(4-pyridyl)-1H—1,2,3-triazole | 130–131 | 40 |
| 10. 1-(p-Chlorophenyl)-5-(3-pyridyl)-1H—1,2,3-triazole | 120–122 | 70 |
| 11. 1-(p-Bromophenyl)-5-(3-pyridyl)-1H—1,2,3-triazole | 136–139 | 70 |
| 12. 1-(p-Fluoro-phenyl)-5-(3-pyridyl)-1H—1,2,3-triazole | 155–156.5 | 80 |
| 13. 1-(3,4-Dichlorophenyl)-5-(3-pyridyl)-1H—1,2,3-triazole | 160–162 | 74 |
| 14. 1-(p-Chlorophenyl)-5-(2-pyridyl)-1H—1,2,3-triazole | — | — |
| 15. 1-(m-Fluorophenyl)-5-(4-pyridyl)-1H—1,2,3-triazole | 87–89 | 33 |
| 16. 1-(m-Bromophenyl)-5-(4-pyridyl)-1H—1,2,3-triazole | 125–126.5 | 50 |
| 17. 1-(m-Tolyl)-5-(4-pyridyl)-1H—1,2,3-triazole | 76–79 | 47 |
| 18. 1-(m-Trifluoromethylphenyl)-5-(4-pyridyl)-1H—1,2,3-triazole | 115–116 | 47 |
| 19. 1-(p-Trifluoromethylphenyl)-5-(3-pyridyl)-1H—1,2,3-triazole | 122–123.5 | 66 |

These compounds were identified through their elemental analyses, characteristic melting point (unlike 1,2,3-triazolines, 1,2,3-triazoles do not decompose at their melting point with vigorous evolution of nitrogen), and NMR spectra, which exhibit a sharp singlet signal in the $\delta 8.0$ region characteristic of the 4-CH proton in the 1,5-substituted-1,2,3-triazoles. The CH signal for the 1,4-substituted triazoles would appear at $\delta < 8$ (Stephan, E., Bull. Soc. Chim. Fr., 7–8 364, 1978).

These compounds were then evaluated in accordance with the methods set forth above for anticonvulsant characteristics. The results are set forth in Table 1 above. As pointed out with respect to Table 1, the compounds demonstrate anticonvulsant activity in either the MES test or the scMet test or both. Compounds of Class I demonstrate this activity at doses of 100 mg/kg or 25 mg/kg without signs of neurological deficit and thus have an estimated protective index of greater than 1.

EXAMPLE 2

One of the compounds, Compound 10, which is 1-(parachlorophenyl)-5-(3-pyridyl)-1H-1,2,3-triazole, was evaluated in further studies to provide additional information as to its general profile of anticonvulsant activity.

Thirty minutes after administration, Compound 10 of this invention exhibited anti-maximal electroshock (MES) at 30 mg/kg and anti-Metrazol (sc Met) activity at 300 mg/kg. Rotorod toxicity was seen in all four animals given 300 mg/kg of the test substance. Four hours after administration, the candidate substance was effective by the MES and scMet tests at 300 mg/kg; one of two animals was also toxic at this dose level. Thus, the profile of anticonvulsant activity of Compound 10 was characterized by the ability to modify maximal electroshock seizure pattern and to elevate the Metrazol seizure threshold in nontoxic doses. Accordingly, the test substance (Compound 10) was subjected to Phase II Anticonvulsant Quantification in Mice i.p., Phase III Toxicity Profile in Mice i.p., Phase IV Anticonvulsant Quantification in Mice p.o., Phase V Antiepileptic Drug Differentiation in Mice i.p., Phase VI Anticonvulsant Quantification in Rats p.o., and Phase VII Chronic Administration in Rats p.o. (tolerance, hexobarbital, and liver microsomal enzyme studies). The results obtained provided the basis to compare the anticonvulsant activity and toxicity of Compound 10 with those of clinically useful antiepileptic drugs.

In these experiments, male albino mice (CF No. 1 strain; 18 to 25 g wt) obtained from Charles Rivers, Wilmington, Mass., and male albino rats (Sprague Dawley, 100 to 150 g wt) obtained from Simonsen, Gilroy, Cal., were used as experimental animals. All animals were allowed free access to both food (S/L Custom Lab Diet-7) and water, except when they were removed from their cages for the experimental procedure.

Compound 10 was compared with four prototype antiepileptic agents (phenytoin, phenobarbital, ethosuximide, and valproate). Compound 10 was administered in the requisite volume of 30% polyethylene glycol 400, whereas phenytoin, phenobarbitol, ethosuximide, and valproate were administered in 0.9% sodium chloride solution. The drugs were administered either orally or intraperitoneally in a volume of 0.01 ml/g body weight in mice and 0.04 ml/10 g in rats. All tests were conducted at the previously determined time of peak drug effect. To determine anticonvulsant potency and toxicity, groups of at least eight mice or rats were tested with various doses of the drug until at least four points were established between the limits of 100% protection or toxicity and 0% protection or toxicity. The dose of drug required to produce the desired endpoint in 50% of animals (ED50) in each test, the dose eliciting evidence of minimal neurological toxicity in 50% of animals (TD50), the 95% confidence interval, the slope of the regression line, and the standard error (S.E.) of the slope were then calculated by means of a computer program written by NINCDS.

The profile of anticonvulsant activity for each substance was established by five tests: one electrical and four chemical. The electrical test employed was the maximal electroshock seizure pattern test. This test measures the ability of the test drug to abolish the hind limb tonic-extensor component of maximal electroshock seizures (mice, 50 mA; rats, 150 mA; 60 Hz, corneal electrodes, 0.2 sec stimulus duration); this amount of current is approximately six times the threshold and reveals the ability of the test substance to prevent seizure spread. The four chemical tests include the subcutaneous Metrazol Seizure Threshold Test (sc Met Test), subcutaneous Bicuculline Seizure Threshold Test (sc Bic Test), subcutaneous Picrotoxin Seizure Threshold Test (sc Pic Test), and the subcutaneous Strychnine Seizure Pattern Test (sc Strych Test). Except for the sc Strych Test, these tests measure the ability of anticonvulsants to afford complete protection against threshold seizures induced by the subcutaneous injection of the CD97 of the convulsant agent. The sc Strych Test measures the ability of the test substance to abolish all tonic components of seizures induced by the subcutaneous injection of the CD97 of strychnine. The sc CD97 of Metrazol, bicuculline, picrotoxin, and strychnine in mice is 85, 2.70, 3.15, and 1.20 mg/kg, respectively; the sc CD97 for Metrazol in rats is 70 mg/kg.

The profile of toxicity for each test drug was established by the following procedures: Firstly, the minimal neurotoxic dose (TD50) was determined by the rotorod procedure at the time of peak neurotoxic effect. When a normal mouse is placed on a knurled rod one inch in diameter rotating at a speed of six rpm it can maintain its equilibrium for long periods of time. Neurological deficit is indicated by inability of the mouse to maintain its equilibrium for one minute in each of three trials on this rotating rod. Neurological deficit in rats is indicated by ataxia, loss of placing response and muscle tone. Secondly, the overt signs and symptoms of toxicity induced by each prototype agent and test substance were determined by giving two mice either 1TD50, 2TD50's, or 4TD50's and observing and testing them 10, 20, and 30 minutes and 1, 2, 4, 6, 8, and 24 hours after drug administration for the onset, intensity, and type of overt toxicity. These observations also provide preliminary information essential for the subsequent determination of the HD50 and LD50. The HD50 represents the median dose at which 50% of animals lose their righting reflex. The 24-hour LD50 represents the median dose which causes death in 50% of the animals within 24 hours.

Except for bicuculline, all convulsant drugs (Metrazol, picrotoxin, and strychnine) administered to mice were dissolved in sufficient 0.9% sodium chloride solution to make a concentration of 0.85%, 0.032%, and 0.012%, respectively. Bicuculline was dissolved in 1 ml of warmed 0.1N HCl with the aid of a micro-mixer and sufficient 0.9% sodium chloride added to make a 0.027% solution; the solution was used 15 to 45 minutes after preparation. Metrazol (3.5%) was administered to rats in a solution of 0.9% sodium chloride.

All convulsants were administered subcutaneously into a loose fold of skin on the back of the neck in a volume of 0.01 ml/g body weight in mice; Metrazol was injected in a volume of 0.02 ml/10 g body weight in rats. The convulsant drugs were administered at the previously determined time of peak anticonvulsant action of the drug under study. Except for picrotoxin-treated animals, the mice (eight animals/group) were then observed for at least 30 minutes for the presence or absence of a seizure. The animals treated with picrotoxin were observed for periods of 45 to 60 minutes for the presence or absence of a seizure. Except for strychnine, absence of a five-second episode of clonic spasms (threshold seizure) was taken as protection. In the case of strychnine, complete abolition of the hindleg tonic extension was taken as protection.

The results obtained in Phase II Anticonvulsant Quantification Studies in Mice i.p., are shown in Table 3. It may be seen from the table that the times of peak effect (TPE) of the five compounds range from 15 minutes to two hours. The TPE of Compound 10 was 60 minutes for the rotorod toxicity test and 30 minutes for the anticonvulsant tests.

With respect to anticonvulsant activity, phenobarbital, Compound 10 of this invention and valproate had significant anticonvulsant activity in nontoxic doses as measured by both the maximal electroshock seizure (MES: ED50's: 21.78, 65.76, and 271.66 mg/kg. respectively) and subcutaneous Metrazol seizure (scMet; ED50's: 13.17, 26.95, and 148.59 mg/kg, respectively) tests. In contrast to the above, phenytoin had significant anti-MES activity (ED50: 9.50 mg/kg) but did not protect against subcutaneous Metrazol seizures. Ethosuximide, on the other hand, was not able to protect mice from maximal electroshock seizures but exhibited significant anti-Metrazol activity in nontoxic doses (ED50: 130.35 mg/kg).

With regard to minimal neurotoxicity, ethosuximide and valproate were the least toxic (TD50's: 440.83 and 425.84 mg/kg, respectively), whereas phenytoin and phenobarbital were the most toxic with TD50's of 65.46 and 69.01 mg/kg, respectively. The Compound 10 of this invention was intermediate in toxicity with a TD50 of 244.51 mg/kg.

by the sc Met test with P.I.'s of 3.38, 2.87, and 5.24, respectively.

Phase III, Toxicity Profile Studies in Mice given 1TD50, 2TD50's and 4TD50's of Compound 10 intraperitoneally, were also carried out on the compounds. The toxicity profile induced by 1TD50 of Compound 10 was characterized by decreased motor activity, rotorod toxicity, ataxia, and decreased respiration. In addition to these symptoms, animals given 2T50's of Compound 10 exhibited cyanosis, muscle relaxation, and loss of righting reflex. Both mice given 4TD50's of Compound 10 of this invention displayed all the symptoms characteristic of those given 1TD50 and 2TD50's of the test drug; however, the symptoms were more intense. Animals given 1TD50 were normal after 24 hours, whereas both mice given 2TD50's were dead after 24 hours; one animal given 4TD50's was dead 4 hours after drug administration and the other was dead at 24 hours. A more detailed qualitative description of the profile of acute toxicity in mice (i.p.) of Compound 10 as well as phenytoin, phenobarbital, ethosuximide, and valproate is shown in Table 4. In addition, the hypnotic dose 50 (HD50) and lethal dose 50 (LD50) of these compounds

TABLE 3

PROFILE OF ANTICONVULSANT ACTIVITY OF INTRAPERITONEALLY ADMINISTERED COMPOUND 10 AND SOME PROTOTYPE ANTIEPILEPTIC DRUGS IN MICE.

| ADD No. Substance | Time of Test (hrs) | Rotorod TD50 (mg/kg) | ED50 (mg/kg) and PI | | | |
|---|---|---|---|---|---|---|
| | | | MES | | sc MET | |
| Compound 10 | 1, ½, ½ | 244.51 (221.82-275.17) [13.86] | 65.76 (51.82-83.19) [5.43] | 3.72* | 26.95 (9.89-55.08) [1.21] | 9.07* |
| Phenytoin | 2, 2, 2 | 65.46 (52.49-72.11) [15.23] | 9.50 (8.13-10.44) [13.66] | 6.89 | No Protection up to 300 | <0.22 |
| Phenobarbital | ½, 1, 1 | 69.01 (62.84-72.89) [24.67] | 21.78 (14.99-25.52) [14.98] | 3.17 | 13.17 (5.87-15.93) [5.93] | 5.24 |
| Ethosuximide | ½, ½, ½ | 440.83 (383.09-485.34) [18.37] | No protection up to 1000 | <0.44 | 130.35 (110.99-150.45) [10.06] | 3.38 |
| Valproate | ¼, ¼, ¼ | 425.84 (368.91-450.40) [20.84] | 271.66 (246.97-337.89) [12.83] | 1.57 | 148.59 (122.64-177.02) [11.84] | 2.87 |

( ) 95% Confidence interval
[ ] Slope, regression line
* Protective Index (P.I.) = TD50/ED50

It may also be seen from Table 3 that the protective indices (TD50/ED50=P.I.) by the MES test range from <0.44 for ethosuximide to 6.89 for phenytoin. The P.I.'s of the remaining three compounds (valproate, Compound 10 of this invention and phenobarbital) are 1.57, 3.72, and 3.17, respectively. The P.I.'s of compounds by the sc Met test range from <0.22 for phenytoin to 9.07 for the compound of this invention. Ethosuximide, valproate, and phenobarbital were also effective are also listed. As shown in the table, the HD50 and LD50 of Compound 10 were not significantly different (525.97 and 569.26 mg/kg, respectively). The HD50 for Compound 10 was significantly higher than that for either phenobarbital (135.45 mg/kg) or phenytoin (178.34 mg/kg), but significantly lower than that for either valproate (885.53 mg/kg) or ethosuximide (850.61 mg/kg).

TABLE 4

PROFILE OF ACUTE NEUROTOXICITY OF INTRAPERITONEALLY ADMINISTERED COMPOUND 10 AND SOME PROTOTYPE ANTIEPILEPTIC DRUGS IN MICE

| ADD No. or Name | Profile of Acute Toxicity, Mice i.p. | | | $\frac{HD50}{LD50*}$ (mg/kg) |
|---|---|---|---|---|
| | 1 × TD50 | 2 × TD50 | 4 × TD50 | |
| Compound 10 | (245 mg/kg) At 1 hr one of two animals exhibited decreased motor activity, ataxia, rotorod toxicity, and decreased respiration. The remaining animal showed only ataxia. Both were normal at 24 hrs. | (490 mg/kg) Both animals had decreased motor activity, ataxia, and rotorod toxicity at 10 min. In addition, decreased respiration was evident at 20 min, and muscle relaxation with cyanosis at 30 min with loss of righting reflex at 2 hrs. One animal regained its righting reflex at 4 hrs. Both animals were dead at 24 hrs. | (980 mg/kg) At 20 min, both animals had decreased motor activity, ataxia, rotorod toxicity, muscle relaxation and decreased respiration with cyanosis. One animal had loss of righting reflex. The other animal lost its righting reflex at 1 hr. One animal was dead at 4 hrs, the remaining animal was dead at 24 hrs. | 525.97 (473.77–564.48) [20.18] <br> 569.26 (520.98–640.59) [14.55] |
| Phenytoin | (65 mg/kg) Increased motor activity, slight ataxia, frequent grooming, nervous behavior, and straub tail, animals were not toxic by the rotorod test. | (130 mg/kg) Mild ataxia, periods of sedation, spasms of arching, rolling, straub tail, ptosis, and respiratory depression. Later, spasms reduced and sedation increased. At 24 hrs, toxicity present, other symptoms less pronounced. | (260 mg/kg) Toxic manifestations identical to 2XTD50. At 1 hr, righting reflex absent, longer periods of sedation, and spasms reduced to head twisting and uncoordianted movements; respiratory depression continued, mice dead at 24 hours. | 178.34 (152.93–195.4) [14.03] <br> 229.61 (216.44–259.10) [15.89] |
| Phenobarbital | (70 mg/kg) Ataxia with increased motor activity followed by sedation and ptosis with one of two animals toxic by the rotorod test up to 4 hrs. | (140 mg/kg) Ataxia with increased motor activity followed by loss of righting reflex, tremors, reflex scratching, ptosis, sedation and some respiratory depression. Both mice regained their righting reflex at 2 hrs and one of two was still toxic by the rotorod test at 8 hrs. | (280 mg/kg) Ataxia with increased motor activity followed by loss of righting reflex, tremors, reflex scratching, ptosis, sedation, anesthesia with analgesia and respiratory depression. Both animals became cold to touch and cyanotic with increased respiratory depression; death occurred at approximately 3 and 6 hrs. | 135.45 (114.90–177.42) [8.41] <br> 264.70 (241.55–285.52) [15.95] |
| Ethosuximide | (440 mg/kg) Uncoordinated motor activity, reflex scratching, respiratory depression, ataxia. | (800 mg/kg) Uncoordinated motor activity, reflex scratching, loss of righting reflex at 4 mins but regained in 20 mins, hypnosis followed at later time intervals by sedation, ataxia, ptosis, vasodilation and diarrhea. | (1760 mg/kg) Uncoordinated motor activity, respiratory depression, hypnosis and anesthesia followed at later time intervals by cyanosis and death at 24 hrs. | 850.61 (751.19–917.93) [16.43] <br> 1752.23 (1607.02–1866.64) [14.75] |
| Valproate | (400 mg/kg) Mild ataxia, with one of two mice toxic by the rotorod test. Appeared normal at the end of 4 hrs. | (800 mg/kg) Ataxia, with both animals toxic by the rotorod test, normal respiration and some sedation. Both animals appeared normal at 4 hrs.) | (1600 mg/kg) Both animals died. 885.53 (At 3XTD50 there was respiratory depression, ptosis, hypnosis but no analgesia. These animals were dead at 4 hrs.) | (820.86–957.04) [12.46] <br> 1104.62 (1021.54–1253.66) [11.41] |

The LD50 (569.26 mg/kg) for Compound 10 was significantly higher than that for either phenytoin (229.61 mg/kg) or phenobarbital (264.70 mg/kg); however, it was significantly lower than that for either valproate (1104.62 mg/kg) or ethosuximide (1752.23 mg/kg).

The anticonvulsant activity and minimal neurotoxic dose (TD50) for Compound 10 as determined by Phase IV studies, Anticonvulsant Quantification in Mice p.o., indicated that the TPE of Compound 10 after oral administration was six hours by the rotorod test and one hour by the anticonvulsant tests. Except for valproate, the four prototype agents exhibited TPE's that were not significantly different from those observed after the intraperitoneal administration of these agents. Valproate had a TPE of one to two hours after oral administration vs one-fourth hour after intraperitoneal administration.

With respect to anticonvulsant activity as measured by the MES test, phenytoin was again the most potent (ED50: 9.04 mg/kg), whereas valproate was the least potent (ED50: 664.80 mg/kg). Compared to phenytoin, phenobarbital was somewhat less potent by the MES test (ED50: 20.09 mg/kg). The test compound (Compound 10) on the other hand, was 1/6 and 1/15 as potent as phenobarbital and phenytoin, respectively, by the MES test with an ED50 of 131.67 mg/kg. When evaluated by the subcutaneous Metrazol threshold test after oral administration, phenobarbital was the most potent (ED50: 12.59 mg/kg) and valproate was the least potent (ED50: 388.31 mg/kg). The other two compounds (Compound 10 and ethosuximide) were essentially equal in potency by the sc Met test with ED50's of 135.67 and 192.21 mg/kg, respectively.

By the oral route of administration in mice, Compound 10, ethosuximide, and valproate were essentially equitoxic (TD50's: 729.08, 879,21, and 1264.39 mg/kg, respectively). Phenytoin and phenobarbital were the most toxic with quite similar TD50's (86.71 and 96.78 mg/kg. respectively).

The P.I. for Compound 10 is 5.54 by the MES test, whereas the P.I.'s for phenytoin, phenobabital, ethosuximide, and valproate are 9.59, 4.82, <0.44, and 1.90, respectively. The P.I. for Compound 10 by the sc Met test is 5.37, whereas those for phenytoin, phenobarbital, ethosuximide, and valproate are <0.29, 7.69, 4.56, and 3.26, respectively. Thus, the P.I. for Compound 10 of this invention by the MES test compares very favorably with the P.I. for phenobarbital (5.54 and 4.82 respectively), whereas the P.I. for Compound 10 by the sc Met test (5.37) is lower than that for phenobarbital (7.69), but higher than that for either ethosuximide (4.56) or valproate (3.26).

The results obtained in Phase V evaluation, Antiepileptic Drug Differentiation in Mice, indicated that the profile of anticonvulsant activity of Compound 10 is characterized by its effectiveness by the sc Met test and ineffectiveness by the sc Bic, sc Pic, and sc Strych tests. Thus, its profile of anticonvulsant action does not resemble that of any of the four prototype agents. Phenobarbital and valproate, on the other hand, were effective by all four anticonvulsant tests. However, it should be noted that valproate was effective against strychnine in nontoxic doses, whereas phenobarbital had to be given in toxic doses in order to protect against this chemical convulsant. Phenytoin, on the other hand, was ineffective against Metrazol, bicuculline, and picrotoxin and was only capable of providing protection in 50% of animals given strychnine. Ethosuximide was effective by the Sc Met, sc Bic, and sc Pic tests, and only protected a maximum of 62% of animals by the Sc Strych test. However, ethosuximide had to be given in toxic doses to protect against sc Bic seizures.

In Phase VI studies, Anticonvulsant Quantification in Rats p.o., it was found that the TPE for Compound 10 in this species after oral administration was two hours by the toxicity test and four hours by the MES and sc Met tests. The TPE of the other four compounds ranged from one-half hour for valproate to five hours for phenobarbital.

With respect to anticonvulsant activity it may be seen that after oral administration in rats, phenobarbital was the most potent by the MES test (ED50: 9.14 mg/kg), whereas valproate was the least potent (ED50: 489.54 mg/kg). The ED50's of phenytoin and Compound 10 by this test were 29.82 and 49.89 mg/kg, respectively. When compared on the basis of the sc Met test, phenobarbital was the most potent (ED50: 11.55 mg/kg) and Compound 10 was the least potent (ED50: 329.18 mg/kg). Ethosuximide and valproate were less potent than phenobarbital by this test with ED50's of 53.97 and 179.62 mg/kg, respectively.

With regard to neurotoxicity, Compound 10 and phenobarbital were essentially equitoxic (44.48 and 61.09 mg/kg, respectively) and ethosuximide and phenytoin the least toxic (TD50's: 1012.31 and >3000 mg/kg, respectively). Valproate was intermediate in toxicity with a TD50 of 280.26 mg/kg.

The P.I.'s by the MES test vary from 0.57 for valproate, <0.84 for ethosuximide, and 0.89 for Compound 10 to >100 for phenytoin. The P.I. for phenobarbital is 6.68. The P.I.'s for compounds active by the sc Met test range from 0.14 and 1.56 for Compound 10 and valproate, respectively, to 18.76 for ethosuximide; the P.I. for phenobarbital by this test is 5.29. Phenytoin is ineffective by this test.

Phase VII studies of Compound 10 included five-day LD3, five-day tolerance studies, and effect of chronic administration on the liver microsomal enzyme system. The five-day oral LD3 of Compound 10 is <300 mg/kg in male rats and >300 mg/kg in female rats. The five-day tolerance studies in rats indicate that significant tolerance occurs within this period of time (MES test: 1 of 8 protected in chronic-treated group; 6 of 8 protected in acute [single dose] control group; hexobarbital sleep time, 15.0±2.0 and 16.3±1.2 min in chronic-treated and acute control group, respectively. This interpretation is further supported by the fact that there were significant increases in cytochrone P-450 (0.988±0.096 vs 0.720±0.054 n moles/mg, p-nitroanisole O-demethylase (0.640±0.098 n moles/mg/min in treated vs 0.261±0.035 in controls), and cytochrome C reductase (219±24 n moles/mg/min in treated vs 157±11 in controls) of chronically treated rats as compared to the acute (single dose) control group.

TABLE 5

QUANTITATIVE TOXICITY PROFILE OF INTRAPERITONEALLY ADMINISTERED COMPOUND 10 AND SOME PROTOTYPE ANTIEPILEPTIC DRUGS IN MICE.

| ADD No. Substance | Time of Test (hrs) | Rotorod TD50 (mg/kg) | ED50 (mg/kg) and PI | | | | |
|---|---|---|---|---|---|---|---|
| | | | MES | sc Met | Bicuculline | Picrotoxin | Strychnine |
| Compound 10 | 1, ½, ¼ | 244.51 (221.82–275.17) [13.86] | 65.76  3.72* (51.82–83.19) [5.43] | 26.95  9.07* (9.89–55.08) [1.21] | No protection up to 300  <0.82* | No protection up to 300  <0.82* | ½ protected at 250; no protection at 300  <0.82* |
| Phenytoin | 2, 2 | 65.46 (52.49–72.11) [15.23] | 9.50  6.89 (8.13–10.44) [13.66] | No Protection up to 300  <0.22 | No Protection up to 100  <0.65 | No Protection up to 100  <0.65 | Maximum 50% protection at 55–100  <0.65 |
| Phenobarbital | ½, 1, 1 | 69.01 (62.84–72.89) [24.67] | 21.78  3.17 (14.99–25.52) [14.98] | 13.17  5.24 (5.87–15.93) [5.93] | 37.72  1.83 (26.49–47.39) [4.07] | 27.51  2.51 (20.88–34.82) [4.79] | 95.30  0.72 (91.31–99.52) [18.51] |
| Ethosuximide | ½, ½, ½ | 440.83 (383.09–485.34) [18.37] | No protection up to 1000  <0.44 | 130.35  3.38 (110.99–150.45) [10.06] | 459.01  3.38 (349.92–635.13) [3.21] | 242.69  1.82 (227.84–255.22) [26.43] | Maximum 62% protection at 250–1000 |

TABLE 5-continued
QUANTITATIVE TOXICITY PROFILE OF INTRAPERITONEALLY ADMINISTERED COMPOUND 10 AND SOME PROTOTYPE ANTIEPILEPTIC DRUGS IN MICE.

| ADD No. Substance | Time of Test (hrs) | Rotorod TD50 (mg/kg) | ED50 (mg/kg) and PI | | | | |
|---|---|---|---|---|---|---|---|
| | | | MES | sc Met | Bicuculline | Picrotoxin | Strychnine |
| Valproate | ¼, ¼, ¼ | 425.84 (368.91–450.40) [20.84] | 271.66 (246.97–337.89) [12.83] 1.57 | 148.59 (122.64–177.02) [11.87] 2.87 | 359.95 (294.07–438.54) [7.51] 1.18 | 387.21 (341.37–444.38) [8.35] 1.10 | 292.96 (261.12–323.43) [11.80] 1.45 |

( ) 95% Confidence interval
[ ] Slope, regression line
* Protective Index (P.I.) = TD50/ED50

TABLE 6
PROFILE OF ANTICONVULSANT ACTIVITY OF ORALLY ADMINISTERED COMPOUND 10 AND SOME PROTOTYPE ANTIEPILEPTIC DRUGS IN MICE AND RATS

| Add No. Substance | Time of Test (hrs) | | TD50 (mg/kg) | | MES-ED50 (mg/kg) | | sc Met-ED50 (mg/kg) | |
|---|---|---|---|---|---|---|---|---|
| | Mice | Rats | Mice | Rats | Mice | Rats | Mice | Rats |
| Compound 10 | 6, 1, 1 | 2, 4, 4 | 729.08 (492.47–1009.17) [3.03] | 44.48 (32.78–62.61) [4.21] | 131.67 (108.90–165.74) [6.04] 5.54\* | 49.89 (31.15–73.15) [2.93] 0.89\* | 135.67 (71.74–210.07) [2.16] 5.37\* | 329.18 (83.41–5690.66) [0.89] 0.14\* |
| Phenytoin | 2, 2, 2 | —, 4, 4 | 86.71 (80.39–96.09) [13.01] | No ataxia up to 3000 | 9.04 (7.39–10.62) [6.28] 9.59 | 29.82 (21.92–38.91) [2.82] <100 | No Protection up to 300 <0.29 | No Protection up to 800 |
| Phenobarbital | 2, 2, 2 | ½, 5, 5 | 96.78 (79.88–115.00) [8.51] | 61.09 (43.72–95.85) [3.00] | 20.09 (14.78–31.58) [5.20] 4.83 | 9.14 (7.58–11.86) [4.12] 6.68 | 12.59 (7.99–11.86) [4.12] 7.62 | 11.55 (7.75–15.00) [4.08] 5.29\* |
| Ethosuximide | 1, ½, ½ | 2, 2, 2 | 879.21 (839.89–933.51) [30.50] | 1012.31 (901.66–1109.31) [15.33] | No protection up to 2000 <0.44 | No protection up to 1200 <0.84 | 192.21 (158.59–438.61) [8.12] 3.26 | 53.97 (45.57–60.85) [9.05] 18.76 |
| Valproate | 2, 1, 1 | 1, ½, ½ | 1264.39 (800–2250) [4.80] | 280.26 (191.32–352.76) [4.63] | 664.80 (191.32–352.76) [4.63] 1.90 | 489.54 (351.14–728.37) [2.90] 0.57 | 388.31 (348.87–438.61) [8.12] 3.26 | 179.62 (146.73–210.35) [8.62] 1.56 |

( ) 95% Confidence interval
[ ] Slope, regression line
* Protective Index (P.I.) = TD50/ED50

TABLE 7
QUANTITATIVE TOXICITY PROFILE OF INTRAPERITONEALLY ADMINISTERED COMPOUND 10 AND SOME PROTOTYPE ANTIEPILEPTIC DRUGS IN MICE.

| ADD No. Substance | Time of Test (hrs) | DOSE 50 (mg/kg) | | |
|---|---|---|---|---|
| | | Lethality | Righting Reflex | Rotorod |
| Compound 10 | 24, 6, 1 | 569.24 (520.98–650.59) [14.55] | 525.98 (473.77–564.48) [20.18] 1.08\* | 244.51 (222.82–275.17) [13.86] 2.33\* |
| Phenytoin | 24, 12, 2 | 229.61 (216.44–259.10) [15.89] | 178.34 (152.93–195.45) [14.03] 1.29 | 65.46 (52.46–72.11) [15.23] 3.51 |
| Phenobarbital | 24, 1, ½ | 264.70 (241.55–285.52) [15.95] | 135.45 (114.90–177.42) [8.41] 1.95 | 69.01 (62.84–72.89) [24.67] 3.84 |
| Ethosuximide | 24, ½, ½ | 1752.23 (1607.02–1866.64) [14.75] | 850.61 (751.19–917.93) [16.43] 2.06 | 44,.83 (383.09–485.34) [18.37] 3.98 |

TABLE 7-continued
QUANTITATIVE TOXICITY PROFILE OF INTRAPERITONEALLY ADMINISTERED COMPOUND 10 AND SOME PROTOTYPE ANTIEPILEPTIC DRUGS IN MICE.

| ADD No. Substance | Time of Test (hrs) | DOSE 50 (mg/kg) | | |
|---|---|---|---|---|
| | | Lethality | Righting Reflex | Rotorod |
| Valproate | 24, ¼, ¼ | 1104.62 (1021.54–1253.66) [11.41] | 885.53 (820.86–947.04) [12.46]   1.25 | 425.84 (368.91–450.40) [20.84]   2.59 |

( ) 95% Confidence interval
[ ] Slope, regression line
\* Protective Index (P.I.) = TD50/ED50

The profiles of anticonvulsant activity of Compound 10 and the four prototype agents after intraperitoneal administration in mice and oral administration in mice and rats are summarized in Tables 5 and 6, respectively. It is seen from Table 5 that, in terms of the profile of anticonvulsant activity, Compound 10 does not resemble any of the four prototype agents. Unlike phenobarbital and valproate, Compound 10 is ineffective in doses up to 300 mg/kg after i.p. administration in mice by the sc Bic, sc Pic, and sc Strych tests, whereas phenobarbital and valproate are effective by these tests. In terms of rotorod toxicity, the Compound 10 is approximately twice as toxic as either ethosuximide or valproate in this species. It may be seen from Table 6 that after oral administration, Compound 10 is approximately 16 times more neurotoxic in rats than it is in mice; likewise, Compound 10 is about 2½ times more potent by the sc Met test in mice than in rats. It should be noted that phenytoin administered orally in higher doses is absorbed only to a limited extent from the gastrointestinal tract of rats. Consequently, no minimal neurotoxicity was observed in this species even in doses up to 3000 mg/kg (see Table 6).

The quantitative toxicity profiles after intraperitoneally administering Compound 10 and the four prototype agents in mice are summarized in Table 7. It may be seen that the times of peak toxicity for phenytoin by the rotorod and righting reflex tests are 2 and 12 hours, respectively, whereas the TPE for Compound 10 by the righting reflex test is 6 hours. The TPE for the other three prototype agents by the rotorod and righting reflex tests range from one-fourth to one hour. This table also shows that the LD50/HD50 and LD50/TD50 ratios for Compound 10 are 1.08 and 2.33, respectively. Thus the ratios between either the minimal toxic dose and the 24-hour lethal dose or the loss of righting reflex does and the 24-hour lethal dose for Compound 10 are lower than those for any of the four candidate substances; hence, the margin between the minimal toxic dose and the 24-hour lethal dose in mice is unusually narrow.

The selectivity exhibited by Compound 10 and the four prototype agents as indicated by the slopes of the regression lines derived from the MES, sc Met, rotorod loss of righting reflex, and 24-hour lethality tests (mice, i.p.) is summarized below:

| | Correlation Between the Slopes of the Regression Lines for Compound 10 and the Prototype Agents | | | | |
|---|---|---|---|---|---|
| Prototype | MES Compound 10 | Sc Met Compound 10 | Rotorod Compound 10 | Right. Reflex Compound 10 | Deaths- 24 hours Compound 10 |
| Phenytoin | * | * | X | * | X |
| Phenobarbital | * | * | * | * | X |
| Ethosuximide | * | * | * | X | X |
| Valproate | * | * | * | * | X |

X Correlates with indicated prototype to a certain extent
\*Does not correlate well with prototype agent.

It may be seen from the above summary that in terms of selectivity of effect as indicated by the slope of the regression lines, Compound 10 resembles phenytoin by the rotorod test; ethosuximide by the righting reflex test; and all the prototype agents by the 24-hour lethality test. In marked contrast, Compound 10 does not resemble any of the prototype agents by either the MES or sc Met tests. The reason Compound 10 does not resemble the prototype agents by the MES test is due to flatter slopes of the regression lines (5.43 for Compound 10 vs 13.66, 14.98, and 12.83 for phenytoin, phenobarbital, and valproate, respectively); similarly, Compound 10 has a much flatter slope by the sc Met test (1.21 for Compound 10 vs 5.93, 10.06, and 11.84 for phenobarbital, ethosuximide and valproate, respectively).

Since all protective indices (P.I.'s) are based on the assumption that the slope of the regression lines (toxicity and activity) are parallel, it is important to note the effect of slope on the safety ration (SR=TD3/ED97) for Compound 10, phenobarbital, and valproate. The safety ratios of these substances are summarized below.

| Parameter | Species & Route Admin. | Substance and Test | | | | | |
|---|---|---|---|---|---|---|---|
| | | Compound 10 | | Phenobarbital | | Valproate | |
| | | MES | sc Met | MES | sc Met | MES | sc Met |
| TD3 | Mice, i.p. | 175 | 175 | 57 | 57 | 345 | 345 |
| ED97 | " | 145 | 900 | 29 | 27 | 380 | 218 |
| Ratio | | 1.2 | 0.2 | 2.3 | 2.5 | 0.9 | 1.6 |
| TD3 | Mice, oral | 173 | 173 | 58 | 58 | 500 | 500 |
| ED97 | " | 275 | 980 | 46 | 38 | 840 | 680 |
| Ratio | | 0.6 | 0.2 | 1.3 | 1.5 | 0.6 | 0.7 |
| TD3 | Rats, oral | 16 | 16 | 14 | 14 | 115 | 115 |
| ED97 | " | 215 | >10000 | 26 | 34 | 1800 | 188 |
| Ratio | | 0.07 | 0.002 | 0.5 | 0.4 | 0.1 | 0.6 |

Safety Ratios* (TD3/ED97) of Compound 10, Phenobarbital, and Valproate

*Ratios less than 1 indicate that 97% protection is obtained only with some minimal neurotoxicity.

The above summary indicates that after intraperitoneal administration of nontoxic doses, the test substance (Compound 10) will protect 97% of mice subjected to the MES test, whereas toxic doses are required to provide this same level of protection by the sc Met test. After oral administration of the test substance in mice and rats, toxic doses are required to protect 97% of animals by either the MES or sc Met test. Moreover, the candidate substance (Compound 10) and the two prototype agents used for comparison of the safety ratios do not provide 97% protection by the MES and sc Met tests in nontoxic doses after oral administration in rats.

For a candidate drug to be useful in man, it should be adequately absorbed after oral administration. The extent of oral absorption can be determined from the ratio of the oral ED50/i.p. ED50 for a desired pharmacologic activity and should be equal to or less than 4 for adequate absorption. The oral TD50/i.p. TD50 and oral ED50/i.p. ED50 ratios for Compound 10 in mice are 2.98, 2.00, and 5.03 by the rotorod MES, and sc Met tests, respectively. This suggests that Compound 10 is adequately absorbed in mice after oral administration.

Chronic studies indicate that Compound 10 is more toxic in male than in female rats. Thus, the estimated five-day LD3 for Compound 10 is <300 mg/kg in male rats and >300 but <1000 mg/kg in female rats. The five-day chronic studies also demonstrate that significant toleance to the anticonvulsant effects of Compound 10 develops in rats within this short period of time. This interpretation is confirmed, not only by the marked difference in response to the MES test (single dose of 50 mg/kg, 6 of 8 rats protected; five daily doses of 50 mg/kg, 1 of 8 protected), but also by the significant increase observed in liver cytochrome P-450 (37%), p-nitroanisole O-demethylase (145%), and cytochrome C reductase (40%).

For a candidate antiepileptic substance to be useful in the treatment of seizure disorders, its experimental profile of action should compare favorably with that of clinically useful antiepileptic drugs. Such a comparison should include not only the anticonvulsant efficacy (ED50), but also the selectivity of toxic and anticonvulsant effects (slope of the dose-effect regression line), toxicity (LD50, HD50, and TD50), protective indices (TD50/ED50), safety ratios (TD3/ED97), absorption characteristics (oral ED50/i.p. ED50 and oral TD50/i.p. TD50) and the margin of safety (single dose five-day LD50/ED50). An analysis of the data for Compound 10, phenobarbital, ethosuximide and valproate shows the relative merits and the disadvantages of Compound 10. The merits of the candidate substance Compound 10 are the favorable safety ratios, TD3/ED97 by the MES test and 24-hour LD50/ED50 by the sc Met test. The disadvantages are related to a lack of selectivity (flat regression line) by the MES test, the unfavorable ratio (TD3/ED97) by the sc Met test, and the toxicity ratios (24-hour LD50/HD50 and 24-hour LD50/TD50).

The invention has been described herein with reference to certain preferred embodiments. However, as obvious variations thereon will become apparent to those skilled in the art, the invention is not to be considered as limited thereto.

I claim:

1. A compound of the following formula:

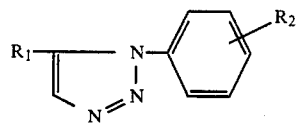

wherein $R_1$ is 4-pyridyl, or 3-pyridyl and $R_2$ is m-methyl, m- or p-fluoro, m-chloro, m- or p-bromo, m- or p-trifluoromethyl, 3,4-dichloro, or 3,5-dichloro.

2. A compound according to claim 1 wherein $R_1$ is 4-pyridyl and $R_2$ is meta-chloro.

3. A compound according to claim 1 wherein $R_1$ is 4-pyridyl and $R_2$ is 3,4-dichloro.

4. A compound according to claim 1 wherein $R_1$ is 4-pyridyl and $R_2$ is 3,5-dichloro.

5. A compound according to claim 1 wherein $R_1$ is 3-pyridyl and $R_2$ is para-chloro.

6. A compound according to claim 1 wherein $R_1$ is 3-pyridyl and $R_2$ is para-bromo.

7. A compound according to claim 1 wherein $R_1$ is 3-pyridyl and $R_2$ is para-fluoro.

8. A compound according to claim 1 wherein $R_1$ is 3-pyridyl and $R_2$ is 3,4-dichloro.

9. A compound according to claim 1 wherein $R_1$ is 4-pyridyl and $R_2$ is meta-fluoro.

10. A compound according to claim 1 wherein $R_1$ is 4-pyridyl and $R_2$ is meta-bromo.

11. A compound according to claim 1 wherein $R_1$ is 4-pyridyl and $R_2$ is meta-methyl.

12. A compound according to claim 1 wherein $R_1$ is 4-pyridyl and $R_2$ is meta-trifluoromethyl.

13. A compound according to claim 1 wherein $R_1$ is 3-pyridyl and $R_2$ is para-trifluoromethyl.

14. A compound according to claim 1 wherein $R_1$ is 4-pyridyl and $R_2$ is para-fluoro.

15. An anticonvulsant composition comprising an effective amount of a compound selected from the group consisting of those of the formulae:

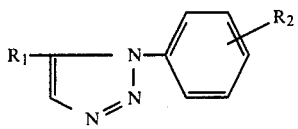

wherein $R_1$ is 4-pyridyl, 3-pyridyl, or 2-pyridyl and $R_2$ is hydrogen, m- or p-methyl, p-methoxy, m- or p-chloro, m- or p-bromo, m- or p-fluoro, m- or p-trifluoromethyl, 3,4-dichloro or 3,5-dichloro and a pharmaceutically acceptable carrier or adjuvent.

16. A composition according to claim 1 wherein $R_1$ is 4-pyridyl and $R_2$ is hydrogen.

17. A composition according to claim 1 wherein $R_1$ is 4-pyridyl and $R_2$ is para-fluoro.

18. A composition according to claim 1 wherein $R_1$ is 4-pyridyl and $R_2$ is para-methyl.

19. A composition according to claim 1 wherein $R_1$ is 4-pyridyl and $R_2$ is para-methoxy.

20. A composition according to claim 1 wherein $R_1$ is 4-pyridyl and $R_2$ is meta-chloro.

21. A composition according to claim 1 wherein $R_1$ is 4-pyridyl and $R_2$ is 3,4-dichloro.

22. A composition according to claim 1 wherein $R_1$ is 4-pyridyl and $R_2$ is 3,5-dichloro.

23. A composition according to claim 1 wherein $R_1$ is 3-pyridyl and $R_2$ is para-chloro.

24. A composition according to claim 1 wherein $R_1$ is 3-pyridyl and $R_2$ is para-bromo.

25. A composition according to claim 1 wherein $R_1$ is 3-pyridyl and $R_2$ is para-fluoro.

26. A composition according to claim 1 wherein $R_1$ is 3-pyridyl and $R_2$ is 3,4-dichloro.

27. A composition according to claim 1 wherein $R_1$ is 2-pyridyl and $R_2$ is para-chloro.

28. A composition according to claim 1 wherein $R_1$ is 4-pyridyl and $R_2$ is meta-fluoro.

29. A composition according to claim 1 wherein $R_1$ is 4-pyridyl and $R_2$ is meta-bromo.

30. A composition according to claim 1 wherein $R_1$ is 4-pyridyl and $R_2$ is meta-methyl.

31. A composition according to claim 1 wherein $R_1$ is 4-pyridyl and $R_2$ is meta-trifluoromethyl.

32. A composition according to claim 1 wherein $R_1$ is 3-pyridyl and $R_2$ is para-trifluoromethyl.

33. A composition according to claim 1 wherein a sufficient amount of the effective ingredient is contained in said composition to provide a dosage amount ranging from about 25 mg/kg to 300 mg/kg.

34. A method for the treatment of convulsive disorders in mammals which comprises administration thereto of an effective dosage amount of a composition of claim 23.

35. A method for the treatment of convulsive disorders in mammals which comprises administration thereto of an effective dosage amount of an anticonvulsant composition comprising an effective amount of a compound selected from the group consisting of those of the formulae:

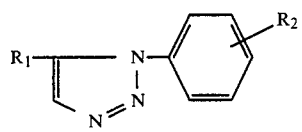

wherein $R_1$ is 4-pyridyl, 3-pyridyl, 2-pyridyl or phenyl and $R_2$ is hydrogen, m- or p-methyl, p-methoxy, m- or p-chloro, m- or p-bromo, m- or p-fluoro, m- or p-trifluoromethyl, 3,4-dichloro or 3,5-dichloro and a pharmaceutically acceptable carrier or adjuvent.

* * * * *